(12) United States Patent
Comtois et al.

(10) Patent No.: US 10,478,861 B2
(45) Date of Patent: Nov. 19, 2019

(54) SYSTEM FOR ANALYZING AND SORTING MATERIAL

(71) Applicants: Hydro Aluminium Rolled Products GmbH, Grevenbroich (DE); Austin AI, Inc., Austin, TX (US)

(72) Inventors: Rick Comtois, Austin, TX (US); John Schindler, Austin, TX (US); Karl Comtois, Austin, TX (US); David Locke, Austin, TX (US)

(73) Assignees: HYDRO ALUMINIUM ROLLED PRODUCTS GMBH, Grevenbroich (DE); AUSTIN AI, INC., Austin, TX (US)

( * ) Notice: Subject to any disclaimer, the term of this patent is extended or adjusted under 35 U.S.C. 154(b) by 36 days.

(21) Appl. No.: 15/361,929

(22) Filed: Nov. 28, 2016

(65) Prior Publication Data

US 2018/0147607 A1  May 31, 2018

(51) Int. Cl.
| B07C 5/342 | (2006.01) |
| G01N 21/63 | (2006.01) |
| B07C 5/344 | (2006.01) |
| B07C 5/36 | (2006.01) |
| B07C 5/02 | (2006.01) |

(52) U.S. Cl.
CPC ............. *B07C 5/342* (2013.01); *B07C 5/344* (2013.01); *B07C 5/368* (2013.01); *G01N 21/63* (2013.01); *B07C 5/02* (2013.01); *B07C 2501/0036* (2013.01)

(58) Field of Classification Search
CPC ..... B07C 7/342; B07C 7/3425; B07C 7/3427; B07C 2501/0036; B07C 5/02; G01N 21/63

See application file for complete search history.

(56) References Cited

U.S. PATENT DOCUMENTS

| 6,252,188 | B1 * | 6/2001 | Zapata | ................... B07C 5/342 |
| | | | | 209/509 |
| 6,753,957 | B1 * | 6/2004 | Graft | ................... G01N 21/718 |
| | | | | 356/318 |
| 7,763,820 | B1 * | 7/2010 | Sommer, Jr. | ............ B07C 5/342 |
| | | | | 209/576 |
| 7,821,634 | B2 * | 10/2010 | Dillon | ....................... G01J 3/02 |
| | | | | 356/318 |

(Continued)

*Primary Examiner* — Joseph C Rodriguez
*Assistant Examiner* — Kalyanavenkateshware Kumar
(74) *Attorney, Agent, or Firm* — Wenderoth, Lind & Ponack, L.L.P.

(57) ABSTRACT

A system (1) for analyzing and sorting material (2) including a feeder (10) for transporting at least one piece of material along a feeding surface (15) towards and onto an upper portion (21) of a chute (20), a sorting device (50), a laser device (30), a spectrometer (40) configured to detect an emission from the piece of material and to produce an output signal corresponding to the emission, and a controller device configured to receive the output signal and to operate the sorting device. The laser device and the spectrometer are both provided on a level below the feeding surface. Also, the laser device is configured to produce a laser beam that can be incident on the piece of material when the piece of material is at least partially protruding from the chute or has fallen off from the chute via the lower edge of the chute and is airborne.

20 Claims, 6 Drawing Sheets

(56) References Cited

U.S. PATENT DOCUMENTS

| | | | |
|---|---|---|---|
| 2003/0132142 A1* | 7/2003 | Kumar | B07C 5/3425 |
| | | | 209/579 |
| 2013/0079918 A1* | 3/2013 | Spencer | B07C 5/3416 |
| | | | 700/223 |
| 2013/0100444 A1* | 4/2013 | Chesner | G01J 3/443 |
| | | | 356/318 |
| 2013/0201481 A1* | 8/2013 | Bamber | G01J 3/00 |
| | | | 356/402 |
| 2014/0166549 A1* | 6/2014 | Ito | B07C 5/02 |
| | | | 209/552 |
| 2014/0262966 A1* | 9/2014 | Cadieux, Jr. | B07C 5/342 |
| | | | 209/3.3 |
| 2017/0205354 A1* | 7/2017 | Buckley | B07C 5/365 |

* cited by examiner

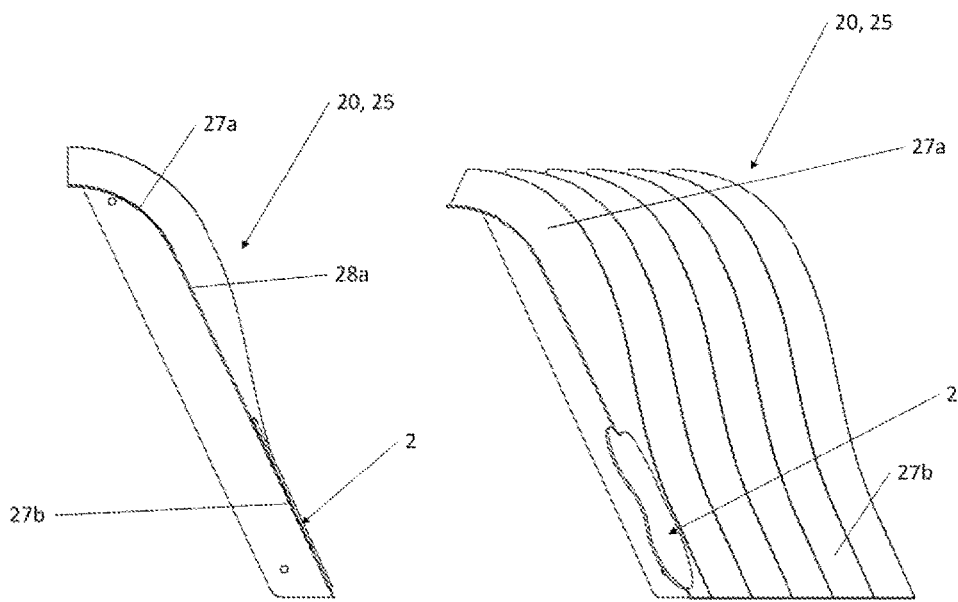
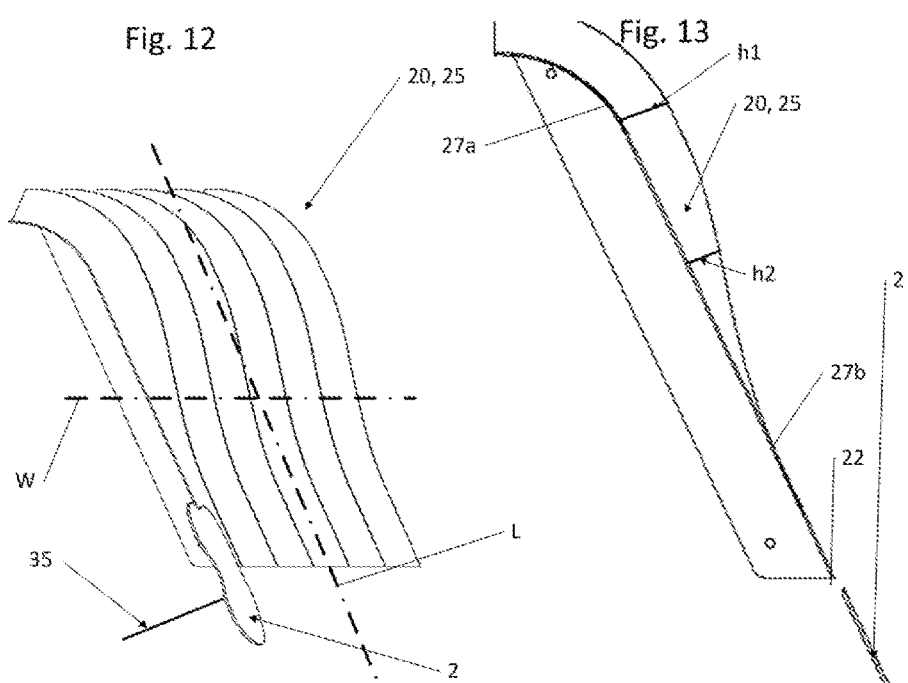
Fig. 12
Fig. 13
Fig. 14
Fig. 15

SYSTEM FOR ANALYZING AND SORTING MATERIAL

BACKGROUND OF THE INVENTION

1. Technical Field

The present invention is generally in the field of analyzing and sorting material pieces of any material, such as glass, metal, plastic, paper etc., and more particularly relates to a system and a method for analyzing and sorting metal pieces such as aluminium scrap pieces using a laser beam.

2. Description of the Related Art

Material such as glass, metal, plastic, paper etc. is often provided as a mixture of pieces having different chemical compositions. For example, aluminium and magnesium metal pieces are often provided as a mixture of different alloys. To use such metal pieces efficiently, e.g. for recycling by remelting, it is necessary to sort a mixture of metal pieces having different compositions according to desired fractions. Using these fractions, desired alloys with defined and desired alloy compositions may be produced by melting the fractions. Accordingly, it is desirable to have an efficient system and method for analyzing and sorting material.

In international application publication WO2015/200111A1 there is disclosed a bulk sampling and laser-targeting system to provide for material identification of a bulk stream of material comprising: a flow chute having a feeder end and an output end, the output end adapted to extend at an angle away from the feeder end such that the flow chute is at an incline and the bulk stream of material flows along the flow chute gravitationally, the flow chute having a substantially concave-shaped configuration including an aperture disposed at a point of maximum concavity of the flow chute that is distal to the feeder end; a LIBS laser system disposed adjacent the aperture and configured to direct a pulsed laser beam through the aperture and into a material flowing through the flow chute, the aperture having a size sufficient to permit the laser beam to pass through to individual particles of the flowing material and to permit radiation from the individual particles to transmit back through the aperture; and a radiation detection device disposed adjacent the aperture and adapted to collect the radiation emitted from the individual particles of material, wherein the radiation detection device is communicatively coupled to the LIBS laser system that includes a spectrometer and a controller, the spectrometer configured to identify a composition of the individual particles flowing in the chute. However, it has been found by the present inventors that the system is ineffective, as it requires an aperture in the chute that may be blocked by scrap.

Further, in international application publication WO2011/154646A1 there is disclosed a method for automatically inspecting and/or sorting in order to analyze and/or distinguish, within a flux, objects belonging to at least two separate categories on the basis of the chemical composition. The method involves providing a substantially single-layer flow of randomly arranged objects passing over a predetermined width; projecting a laser flux that is shaped within an analysis area having the objects passing through; collecting and shaping the detection signals corresponding to the responses output by each object affected by the laser flux; processing and assessing the collected and shaped detection signals, synchronized with the projection of the laser flux, by means of an adapted analysis device that makes it possible to distinguish between the objects. Said method is characterized in that it also involves: dividing the original incident laser flux into a plurality of collimated or focused secondary beams and simultaneously applying the latter at points spaced apart and distributed within the analysis area; and simultaneously collecting, in parallel, the detection signals generated by each secondary beam on contact with an object, item, or piece within the analysis area. However, said method is considered by the present inventors to be inefficient for sorting scrap, as objects that overlap or are very close together cannot be sorted efficiently. For instance, it has been found by the present inventors that metal scrap pieces often stick together resulting in inefficient analysis and sorting. Further, by dividing the laser flux into a plurality of secondary beams, the energy density or energy over time on each piece may become too small to conduct a proper element analysis. Further, while it is mentioned in the claims, the document does not describe the actual sorting of aluminium scrap into fractions in an enabling manner and is therefore not suitable for sorting scrap metal pieces.

SUMMARY OF THE INVENTION

According to an aspect, the invention may provide a system for analyzing and sorting material comprising a feeder means for transporting at least one piece of material along a feeding surface towards and onto an upper portion of a chute, the chute wherein the piece of material is slidable on the chute and off the chute via a lower edge of the chute, a sorting device, operable to sort the piece of material, such as paper, plastic, glass, metal and/or other pieces, according to at least two fractions, a laser device configured to generate a laser beam that, when the laser beam is incident on the piece of material, can produce an emission from the piece material, a spectrometer configured to detect the emission from the piece of material and to produce an output signal corresponding to the emission and indicative of the chemical composition of the piece of material, and a controller device configured to receive the output signal and to operate the sorting device based on the output signal and at least one sorting criterion, wherein the laser device and the spectrometer are both provided on a level below the feeding surface, and wherein the laser device is configured to produce a laser beam that can be incident on the piece of material when the piece of material is at least partially protruding from the chute over the lower edge of the chute or has fallen off from the chute via the lower edge of the chute and is airborne. According to embodiments, the system may be configured such that the laser beam is incident only on pieces of material that are airborne. According to embodiments, the system may be configured such that the laser beam is incident only on a piece of material that protrudes over the lower edge of the chute while it is still supported by the chute.

The feeder means may be configured to change relative distances between pieces of material on the feeding surface while transporting the pieces of material.

The feeder means may comprise at least one vibration feeder.

The feeder means may comprise at least an upstream vibration feeder and a downstream vibration feeder, wherein the upstream vibration feeder is configured to transport a piece of material towards and onto the downstream vibration feeder, wherein the downstream vibration feeder transports the piece of material towards and onto the upper portion of the chute, wherein the feeding surface of the upstream vibration feeder is provided on a higher level than the feeding surface of the downstream vibration feeder, and wherein the upstream vibration feeder is operated at a lower vibration frequency and/or amplitude than the downstream vibration feeder. At least the feeding surface of the downstream vibration feeder may have a corrugated shape that forms a plurality of channels.

The system may optionally not comprise any beam separation means or mirror means in the path of the laser beam between the laser device that generates the laser beam and the piece of material on which the laser beam is incident.

The at least one piece of material may be a piece of metal scrap. The piece of metal scrap may be a piece of 5xxx or 6xxx alloy series aluminium having a diameter of more than 5 mm to 200 mm, e.g, more than 10 mm and less than 150 mm, e.g. more than 10 mm and less than 40 mm.

The laser device and the spectrometer may form a LIBS (laser induced breakdown spectroscopy) system and may be housed in a common housing.

The laser beam, after being generated by the laser device, may extend upwards with an angle of between 0 and 90 degree, optionally between 40 and 70 degree, with respect to a horizontal line.

The laser beam may not propagate through the chute, e.g. an opening or aperture thereof.

The chute may be implemented as a guiding slide that defines a length direction between the upper portion and the lower edge and a width direction perpendicular thereto and comprises at least one channel along which the at least one piece of material is slidable from the upper portion to the lower edge, wherein the channel in a section along the length direction comprises a convex portion in the upper portion followed by a straight portion between the convex portion and the lower edge, and wherein the channel in a section along the width direction in the upper portion has a profile shape with a trough and two side walls having a first height, and wherein the channel in a section along the width direction between the upper portion and the lower edge has a profile shape with a trough and two side walls having a second height, wherein the first height is larger than the second height. The channel in a section along the width direction through the lower edge of the chute may have a straight shape that is at least substantially horizontal.

The sorting device may be configured to impart an impulse on the at least one piece of material by using compressed air, and the system may optionally further comprise a separator provided spatially between two bins or conveyors corresponding to two of the at least two fractions.

According to a further aspect, the invention may provide a method for analyzing and sorting material comprising supplying at least one piece of metal to and onto a feeding surface of a feeder means, transporting the at least one piece of metal on the feeding surface towards and onto an upper portion of a chute using the feeder means, sliding the at least one piece of metal on the chute from the upper portion of the chute towards an lower edge of the chute by at least partially using a gravitational force, providing a laser beam such that the laser beam is incident on a part of the at least one piece of metal that is protruding over the lower edge of the chute, or such that the laser beam is incident on the at least one piece of metal when the at least one piece of metal has fallen from the chute via the lower edge of the chute, generating an emission from the at least one piece of metal using the laser beam, detecting the emission, determining to which fraction of at least two fractions the at least one piece of metal corresponds based on the detecting and at least one sorting criterion, sorting the piece of metal into one of the at least two fraction based on the determining. The piece of material may be aluminium scrap material and the method may further comprise pre-treating the aluminium scrap material by sorting such that the aluminium scrap material has a maximum diameter between 5 mm and 200 mm, e.g. between 10 mm and 150 mm, e.g. between 10 mm and 40 mm. The transporting may comprise transporting at least two pieces of material and changing a relative distance between the at least two pieces of material on the feeding surface while transporting the at least two pieces of material.

BRIEF DESCRIPTION OF THE DRAWINGS

FIGS. 8 to 15 show detailed schematic views of a chute implemented as a guiding slide according to the invention.

DETAILED DESCRIPTION OF THE INVENTION

In the following, various exemplary embodiments of the invention are described with reference to the figures. Various aspects of the subject matter described herein may be implemented in any of numerous ways, as the subject matter described herein is not limited to a particular manner of implementation. Specific exemplary implementations, uses and applications are provided for illustrative purposes and are not limiting the invention as defined in the claims.

Herein, terms that are indicative of a relative height or position, such as above or below or the like, are defined with respect to gravity, i.e. with respect to the vertical direction. That is, a first object that is herein described to be "above" a second object may be farther away from the center of the earth than the first object.

Figure 1:
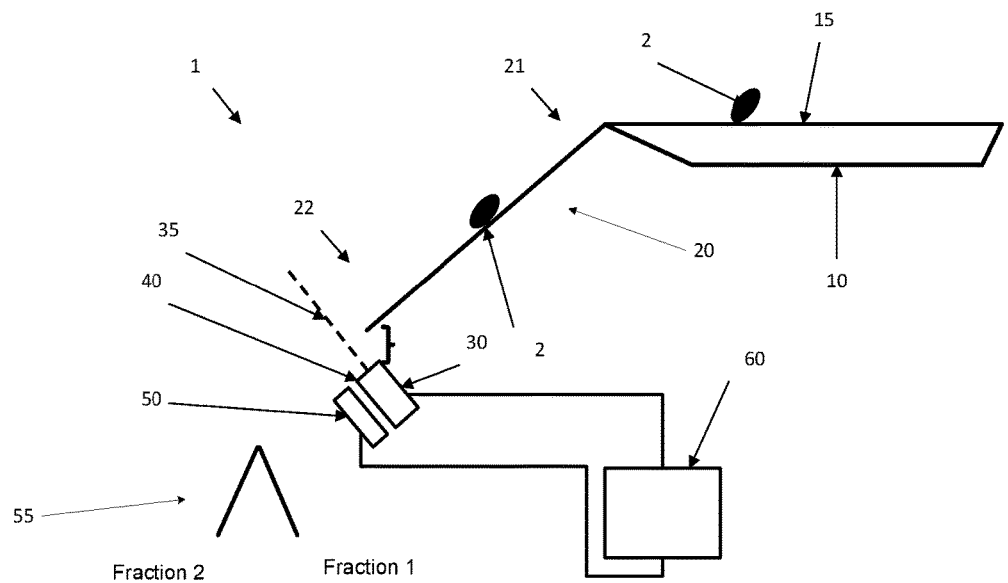
FIG. 1 schematically shows an embodiment of a system according to the invention.

With reference to FIG. 1, the system 1 for analyzing and sorting pieces of material 2 according to the invention may comprise a feeder means 10 for transporting at least one piece of material 2 along a feeding surface 15 towards and onto an upper portion 21 of a chute 20.

The feeder means 10 may be implemented by a feeder which can separate pieces of material 2 that are provided on a feeding surface 15 thereof. That is, the feeder means 10 may be configured to change (e.g. increase) a relative distance of pieces of material 2 that are provided on the feeding surface 15 thereof resulting in singulation and separation of the pieces of material 2. The feeder means 10 may for example be implemented by one or more, e.g. two, vibration feeder as is shown further below. It has been found that best analyzing and sorting results are achieved when the feeder means 10 is configured to separate/singulate pieces of material 2, i.e. change the relative distances between pieces of material 2 on the feeding surface 15. Belt conveyors and similar devices that cannot change a relative distance of objects transported therewith have found to be inefficient for sorting and analyzing pieces of material 2 using a system 1 as described herein. For example, scrap aluminium pieces may stick together and form agglomerates that need to be broken up/separated before leaving the feeding surface 15 in downstream direction in order to perform efficient analyzing and sorting. At least a downstream end of the feeding surface 15 (e.g. an end that is neighboring the chute 20) may have a corrugated shape.

The system 1 according to the invention may comprise a pretreatment means provided upstream of the feeder means 10. Said pretreatment means may be configured to only forward pieces of material 2 towards the feeder means 10 that have a certain size or composition. For example, when the system 1 is configured to analyze and sort copper alloys, the pretreatment means may comprise a magnet removing magnetizable material, such as iron and nickel, from the pieces of material 2 which are fed to the feeding surface 15 of the feeder means 10. When the system 1 is configured to analyze and sort metal, e.g. aluminium alloys such as 5xxx and 6xxx aluminium scrap material, the pretreatment means may be configured to only forward pieces of material having a diameter of e.g. between 5 mm and 200 mm, e.g. between 10 mm and 150, e.g. between 0 mm and 110 mm, e.g between 10 mm and 40 mm, to the feeding surface 15 of the feeder means 10. It has been found that then efficient analysis and sorting of 5xxx from 6xxx aluminium alloys can get carried out, as the system 2 according to the invention has an improved analyzing and sorting performance, in particular with respect to throughput while maintaining good analysis and sorting quality, when the diameter of the pieces of material 2 is 10 mm or larger, preferably 40 mm or larger, and 150 mm or smaller, preferably 110 mm or smaller. The pretreatment means may for example comprise one or more sieves or screens, e.g. one that removes pieces having a diameter smaller than 10 mm from the pieces of material 2 and one that removes pieces having a diameter larger than 150 mm from the pieces of material 2.

The system 1 may further comprise the chute 20, wherein the piece of material 2 may be slidable on the chute 20 and off the chute 20 via a lower edge 22 of the chute 20. A driving force for a piece of material 2 may be at least partially, e.g. fully, provided by gravity.

The feeder means 10 may transport a piece of material 2 along the feeding surface 15 thereof towards and onto an upper portion 21 of the chute 20. If there is more than one piece of material 2 provided on the feeder surface 15, the feeder means 10 may separate/singulate these pieces so that they are transported sequentially and piece after piece onto the upper portion 21 of the chute 20.

After reaching the upper portion 21 of the chute 20, a piece of material 2 may slide downwards along the chute 20 towards the lower edge 22 of the chute 20 at least partially driven by gravity. While the chute 20 may be operably connected with the feeder means 10 and may e.g. vibrate with the feeder means 10, if it is implemented as a vibration feeder, the chute 20 may also be separate from the feeder means 10. That is, the chute 20 may be stationary and non-vibrating. If the chute 20 is stationary and non-vibrating, the movement of piece of material 2 from the upper portion 21 of the chute 20 towards the lower edge 22 of the chute 20 may be fully driven by gravity. The upper portion 21 of the chute may correspond to an upper edge of the chute 20 or to a portion of the chute 20 that has a distance from the upper edge of the chute 20 and is neighboring the upper edge of the chute 20.

When the piece of material 2 reaches the lower edge 22, it may slide over the lower edge 22 and may fall from the chute 20 via the lower edge 22 thereof.

The system 1 may further comprise a laser device 30 configured to generate a laser beam 35 that, when the laser beam 35 is incident on the piece of material 2, can produce an emission from the piece of material 2.

The system 1 may further comprise a spectrometer 40 configured to detect the emission from the piece of material 2 and to produce an output signal corresponding to the emission. Further, a controller device 60 configured to receive the output signal and to operate the sorting device 50 based on the output signal and at least one sorting criterion may be provided with the system 2.

The laser device 30 and the spectrometer 40 both may be arranged, with respect to the vertical direction, on a level below the feeding surface 15. When the feeding surface 15 is inclined or has several height levels, "on a level below the feeding surface" may, according to embodiments, refer to the lowest feeding surface 15.

The laser device 30 and the spectrometer 40 according to embodiments both may be arranged, with respect to the vertical direction, on a level below the upper portion 21 of the chute 20. The laser device 30 and the spectrometer 40 according to embodiments both may be arranged, with respect to the vertical direction, on a level below the lower edge 22 of the chute 20. With respect to the horizontal direction, the laser device 30 and the spectrometer 40 may, according to embodiments, both be (e.g. at least partially) arranged under the chute 20

The laser device 30 may be arranged and configured to produce a laser beam 35 that is or can be incident on the piece of material 2 when the piece of material is at least partially protruding from the chute 20 over the lower edge 22 of the chute 20 or when the piece of material 2 has fallen from the chute 20 via the lower edge 22 of the chute 20 and is airborne or "free falling".

The laser device 30 may be configured such that the laser beam 35 produced by the laser device 30 extends upwards with an angle of between 0° to 90° with respect to an horizontal line. According to embodiments, the laser device 30 may be configured such that the laser beam 35 produced by the laser device 30 extends upwards with an angle of between 40° to 80° with respect to an horizontal line. With respect to the vertical direction, the laser device 30 and the spectrometer 40 may for example be arranged between the upper portion 21 and the lower edge 22 of the chute 20.

Depending on the setup of the system 1 and the size of the piece of material 2, the system 2 may be configured such that the laser beam 2 is incident on the piece of material 2 when it protrudes over the lower edge 22 of the chute but is still supported by the chute 20 or when it has fallen from the chute 20 via the lower edge 22 of the chute 20 and is airborne.

The laser device 30 and the spectrometer 40 may form a system for LIBS (laser-induced breakdown spectroscopy). The laser device 30 is configured to produce a laser beam 35 of sufficient power and diameter so that a plasma suitable for analysis by the spectrometer 40 is generated. If the piece of material 2 is aluminium or an aluminium alloy, the laser may for example have a energy of between 1 and 200 mJ and a beam diameter of between 1 and 5 mm when the laser beam 35 exits the laser device 30. Along the beam path, the laser beam 35 may be convergent when it exits the laser device 30 and divergent after a focus point of the laser beam 35. The system 1 may be configured such that the focus point of the laser beam 35 has a distance of between 1 cm and 10 cm, e.g. 1 cm and 5 cm, from the lower edge of the chute 20. The system 1 may be configured such that the focus point of the laser beam 35 lies on a ballistic parabola/curve of the pieces of material 2 exiting the chute 20 via the lower edge 22 thereof.

According to the invention, the laser beam 35 is not diverted or divided between the laser device 30 and the point on which it hits a piece of material 2. That is, according to embodiments of the invention, there is optionally no beam splitter or mirror provided between the laser device 30 and the piece of material 2 that is hit by the laser beam 35 during operation of the system 1. In other words, a specific point in the path of the laser beam 35 has, when the laser device 30 is generating a laser beam 35, constantly the same power as a start point of the laser beam 35 (the point on which the laser beam 35 exits the laser device 30), and the optical path of the laser beam 35 after exiting the laser device 30 can be described by a straight line. The system 1 may be configured such that the laser beam 35 and the chute 20 do not intersect. That is, according to the invention, the laser beam 35 is not extending through an opening or aperture in the chute 20. The inventors have found that such an opening in a chute can get clogged by pieces of material 2 or dust or, if the opening or aperture is covered by a material that is transparent for the laser beam 35, reduce the power of the laser beam 35.

When the laser beam 35 is incident on a piece of material 2, the laser beam 35 may interact with the piece of material 2 to generate an emission form the piece of material 2. Said emission may be indicative of the chemical composition of the piece of material 2. When the laser device 30 and the spectrometer 40 form a system for LIBS, the emission may comprise a plasma. The spectrometer 40 may detect the emission, e.g. by detecting electromagnetic radiation from the emission, and generate an output signal corresponding to the emission. That is, the output signal of the spectrometer 40 may correspond to the chemical composition of the piece of material 2 on which the laser beam 35 is incident.

For example, the laser device 30 may comprise a Nd:YAG solid-state laser device. The Nd:YAG laser device may generate energy in the near infrared region of the electromagnetic spectrum, with a wavelength of about 1064 nm. The pulse duration may be about 10 ns to generate a power density which can exceed 1 GW·cm-2 at the focus point. The laser device 30 may for example generate a laser beam 35 having a frequency of 50 kHz or more. Other types of laser devices may be used as well, for example laser devices of the Excimer (Excited dimer) type that generate energy in the visible and ultraviolet regions.

The spectrometer 40 may for example comprise a chromator, such as monochromator (scanning) or a polychromator (non-scanning), and a detector, such as a photomultiplier or CCD detector. The monochromator may for example be of the Czerny-Turner type. The polychromator may for example be of the Echelle type. A monochromator of the Czerny-Turner type can also be used to disperse radiation from the emission onto a CCD, effectively making the monochromator of the Czerny-Turner type a polychromator. A spectrometer 40 comprising a polychromator allows simultaneous acquisition of the entire wavelength range of interest with respect to the pieces of material 2 that are to be sorted and analyzed. The spectrometer 40 may have a well depth of approximately 62500 electrons.

The spectrometer 40 collects electromagnetic radiation from the emission to detect emission lines for chemical elements. The response of the chromator of the spectrometer 40 may typically be from 1100 nm (near infrared) to 170 nm (deep ultraviolet), which may correspond to the range detectable by the CCD detector. It is thought that all elements have emission lines within this wavelength range. The spectrometer 40 may also comprise a delay generator, which may control the response time of the detector to allow efficient temporal resolution of the electromagnetic spectrum of the emission.

The spectrometer 40 may further be configured to generate the output signal that is indicative of the properties of the emission from the piece of material 2 and therefore is indicative of the chemical composition of the piece of material 2.

The system 1 may further comprise a controller device 60 that is operably connected with the spectrometer 40 to receive the output signal form the spectrometer 40. The controller device 60 may for example be implemented as an embedded system using a RISC CPU (such as an ARM CPU) or a CISC CPU (such as an x86 CPU) or for example as a standard PC that is compatible to the Microsoft Windows operating system. The controller device 60 may for example be connected wirelessly (e.g. via Bluetooth or WLAN) with the spectrometer 40 or non-wirelessly, e.g. via Ethernet, USB, Thunderbolt or a serial or parallel data connection. The controller device 60 may also be connected to the spectrometer, e.g. the detector thereof, via a bus system such as I2C, SPI, ISA, PCI or the like. A data exchange via OPC UA or other protocols may be used.

The controller device 60 may be configured to compare the output signal of the spectrometer 40 with a sorting criterion S1 provided with (e.g. stored in) the controller device 60. Based on the result of the comparison, the controller device 60 may determine whether the piece of material 2 is to be sorted into a specific fraction, e.g. into a first fraction or a section fraction. For example, if the system 1 is configured to separate scrap of 5xxx series aluminium from 6xxx series aluminium, the sorting criterion S1 may correspond to a specific amount of Si (silicon), e.g. to 0.5 wt-% Si. In this example, if the output signal from the spectrometer 40 corresponds to 0.4 wt-% Si in the piece of material 2, it is determined that the piece of material 2 is to be part of the first fraction, and if the output signal from the spectrometer 40 corresponds to 0.5 wt-% Si or more in the piece of material 2, it is determined that the piece of material 2 is to be part of the second fraction. The controller device 60 may be configured to use more than one sorting criterion, e.g. two (S1, S2), three (S1, S2, S3), four (S1, S2, S3, S4) and more (S1, . . . , Sn) sorting criteria. For example, the controller device 60 may in addition to the sorting criterion corresponding to Si content (S1) also apply a sorting criterion corresponding to the Mg (magnesium) content (second sorting criterion S2) and a sorting criterion corresponding to the Mn (manganese) content (third sorting criterion S3). Each sorting criterion may have an associated weighting factor a1, a2, a3, . . . , an that is previously adjusted according to the compositions of the pieces of material 2 that are to be analyzed and sorted.

The system 1 may further comprise a sorting device 50 that is operable to sort the piece of material 2 according to at least two fractions F1, F2. Sorting according to different fractions F1, F2, F3, . . . , Fn may refer to diverting a piece of material 2 into a corresponding basket/bins or onto a corresponding conveyor, e.g to transport material to storage or further processing or the like.

The sorting device 50 may for example be connected to the controller device 60 wirelessly (e.g. via Bluetooth or WLAN) or non-wirelessly, e.g. via Ethernet, USB, Thunderbolt or a serial or parallel data connection. The controller device 60 may also be connected to the sorting device 50 via a bus system such as I2C, SPI, ISA, PCI or the like. A data exchange via OPC UA or other protocols may be used.

The sorting device 50 may be controlled by the controller device 60 based on the result of the determining into which fraction a piece of material 2 should be sorted in.

The sorting device 50 may be configured to selectively impart an impulse on a piece of material 2 after it has fallen from the lower edge 22 of the chute 20 and is airborne based on chemical the composition of the piece of material 2 as determined by the controller device 60 using the output signal of the spectrometer 40. That is, the sorting device 50 may be controlled by the controller device 60. For example, if it is determined by the controller device 60 based on a least one sorting criterion that a piece of material 2 is to be sorted according to a second fraction F2 out of two fractions F1, F2, the sorting device 50 may impart an impulse on the piece of material if it is determined by the controller device 60 that the piece of material 2 belongs to the second fraction F2. The trajectory of the piece of material 2 after it has fallen from the chute 20 is changed by the impulse imparted by the sorting device 50 so that the piece of material is sorted according to the second fraction F2. For example, the piece of material 2 may be diverted into a second bin or onto a second conveyor device (not shown) using the sorting device 50. On the other hand, if it is determined by the controller device 60 that a piece of material 2 should be part of the first fraction F1, the sorting device 50 may be controlled by the controller device 60 such that it imparts a different impulse (e.g. an impulse with a different strength and/or direction) or no impulse (so that the piece of material 2 follows its normal trajectory) on the piece of material 2, such that the piece of material 2 is sorted according to the first fraction F1.

When pieces of material 2 are to be sorted according to two or more fractions, different impulses (impulses having different strengths and/or different directions) may be used to divert the pieces of material 2, wherein the impulse corresponding to a specific fraction may be zero, so that the piece of material 2 follows its normal trajectory as determined by gravity and aerodynamics. This may allow the system to operate 1 more efficiently.

The sorting device 50 may for example be implemented as an air nozzle, an air pump or a blower ("air gun") or the like configured to emit shots of air to impart an impulse on pieces of material 2 that have fallen from the lower edge 22 of the cute 20 and are airborne. The sorting device 50 may also be a mechanical sorting device that imparts an impulse on the piece of material 2 via a direct contact between a part of the mechanical sorting device 50, such as a paddle or lever or ramp, and the piece of material 2. However, the sorting device 50 according to the invention is not particularly limited.

Figure 2:
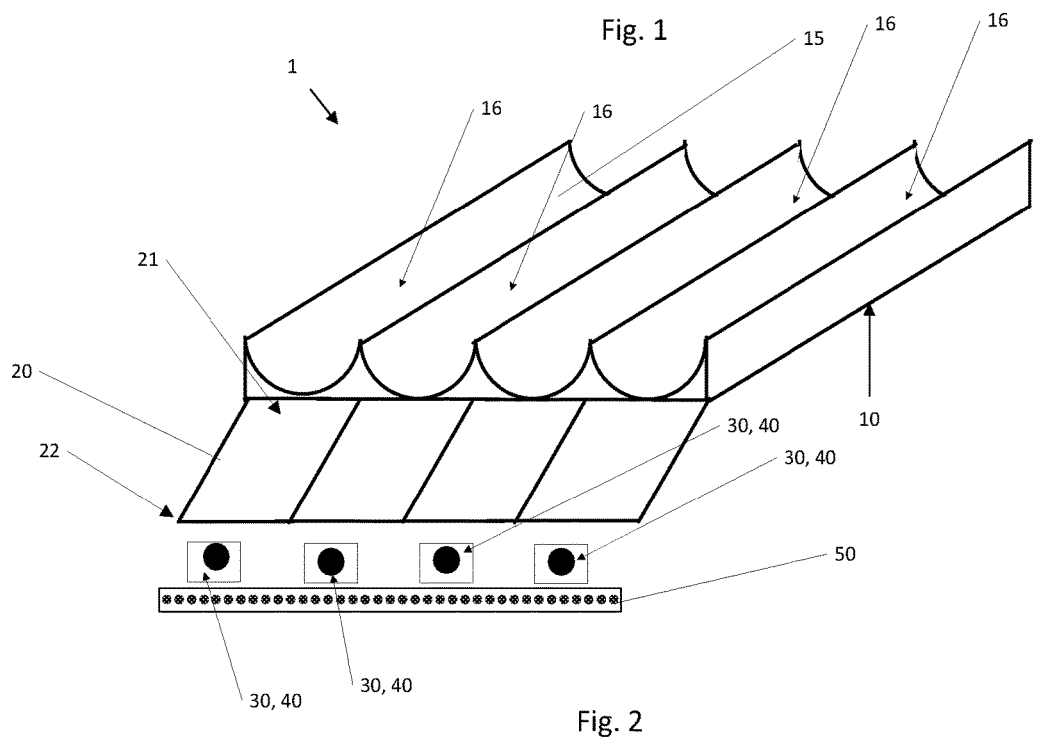
FIG. 2 schematically shows a partial view of system according to the invention configured for parallel analysis and sorting.

As is schematically shown in FIG. 2, the system 1 according to the invention may be configured to analyze and sort more than one piece of material 2 simultaneously. For example, the system 1 may comprise more than one laser device 30 and more than one spectrometer device 40. The laser devices 30 and spectrometers 40 may be arranged pairwise (one laser device 30 and one corresponding spectrometer 40) in a direction perpendicular to a transportation direction of the feeder means 10, i.e. in a width direction.

The chute 20 may have a correspondingly extended width so that a piece of material 2 can be transported to each of the laser device/spectrometer pairs 30, 40. The sorting device 50 may also be configured to sort more than one piece of material 2 simultaneously. The sorting device 50 may for example comprise at least as many paddles, levers or ramps as there are pairs of laser device 30 and spectrometer 40. If the sorting device 50 is implemented as an air nozzle, an air pump or a blower ("air gun") or the like, it may comprise at least as many selectively controllable (e.g. by a valve) air outlets as there are pairs of laser device 30 and spectrometer 40.

Figure 4:
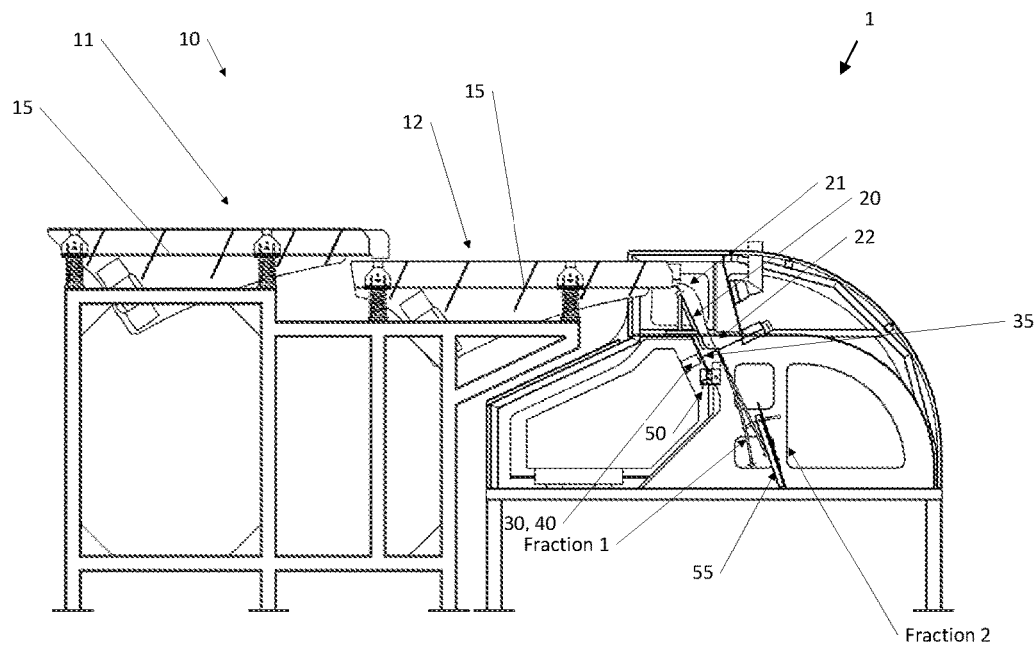
FIG. 4 shows a schematic sectional view of a system according to an embodiment of the invention.
Figure 5:
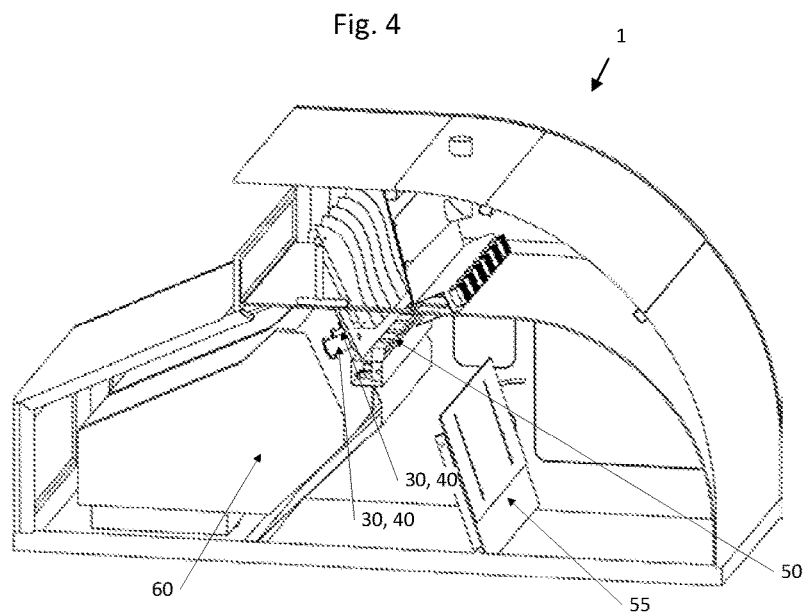
FIG. 5 shows a perspective sectional view of a system according to an embodiment of the invention.
Figure 6:
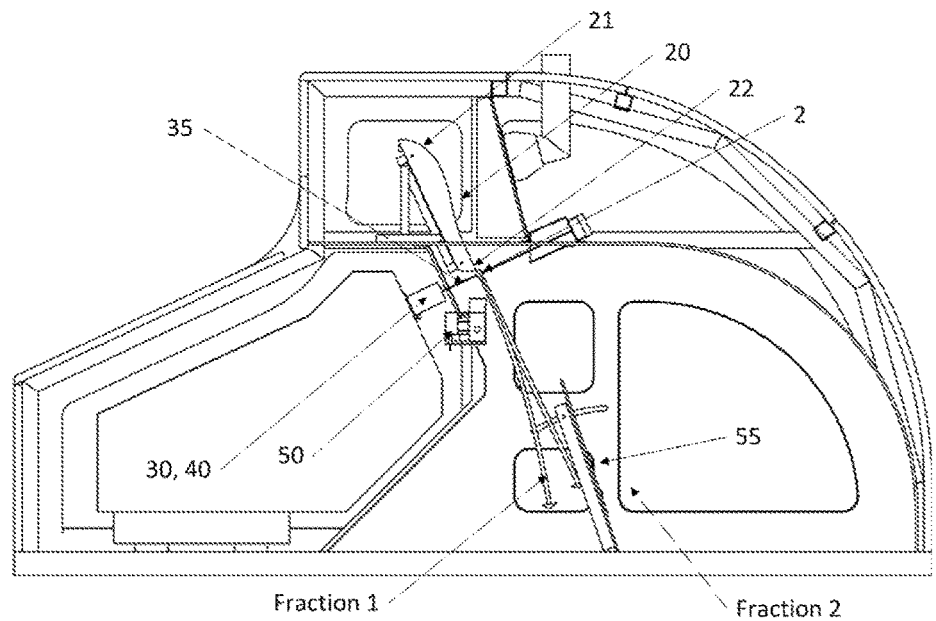
FIG. 6 shows a partial sectional view of a system according to an embodiment of the invention.

Optionally, as is e.g. shown in FIGS. 1, 4, 5 and 6, the system 2 may comprise a splitter 55, e.g. when the sorting device 50 is implemented as an air gun or the like. The splitter 55 may serve as a physical threshold or boundary between the fractions F1 and F2 and may improve sorting performance. The splitter 55 may be adjustable. As shown in FIGS. 4, 5 and 6, the splitter 55 may for example be implemented as a hinged plate structure having an adjustable angle with respect to the vertical plane that is provided spatially between the first fraction F1 and the second fraction F2, e.g. the bins or conveyor belts corresponding to the fractions F1 and F2. For example, when a piece of material 2 is to be sorted into the second fraction F2, it may receive an impulse such that it is diverted over the splitter 55 (to the downstream side of the splitter 55) and into the second fraction F2, and when a piece of material 2 is to be sorted into the first fraction F1, it may e.g. receive no impulse and remain on the side of the splitter 55 that is facing the chute 20. An angle of the hinged plate structure may be adjusted according to the type and the weight of the piece of material 2 to be sorted as is schematically indicated in FIGS. 4, 5, 6 by rotating the plate structure around a hinge. Further, a length of the plate structure between the hinge and a free end of the plate structure may be adjustable, e.g. when the plate structure is implemented by two plates that are selectively movable relative to each other, according to the type and the weight of the piece of material 2 to be sorted. While it has been found that the splitter 55 may increase efficiency of the system 1 according to the invention, it is an optional part.

The laser device 30 and the spectrometer 40 may be provided in a common housing. This allows several sets/pairs of laser device 30 and spectrometer 40 to be efficiently provided in a respective common housing along the width direction of the chute 20. Optionally, the controller 60 may also be provided in the common housing. When the system 1 comprises several common housings each comprising a laser device 30 and a spectrometer 40, the controller 60 may be provided in one of these common housings, e.g. a common housing that is provided on an outermost position in the width direction.

To facilitate the transport of a piece of material 2 to each of the pairs of laser device 30 and spectrometer 40, the feeding surface 15 of the feeder means 10 may have a corrugated shape when seen in section in the width direction (a direction generally perpendicular to the transport direction of the feeder means 10). Said corrugated shape may for example comprise U-shapes or V-shapes arranged next to each in the width direction as is schematically shown in FIG. 2. Said corrugated shape may form several channels 16 and allows it to efficiently separate pieces of material 2 and feed them to the pairs of laser device 30 and spectrometer 40. The corrugated shape may be configured so that it forms as many channels 16 as there are pairs of laser device 30 and spectrometer 40.

While the system 1 shown schematically in FIG. 2 comprises four pairs of laser device 30 and spectrometer 40 and correspondingly four channels 16 formed by the corrugated feeding surface 15, the system 1 according to the invention may also comprise only one pair, or may comprise any other number of pairs, such as two, three, five, six, seven, eight or more. The maximum number of pairs per system 1 according to the invention is not limited.

Figure 3:
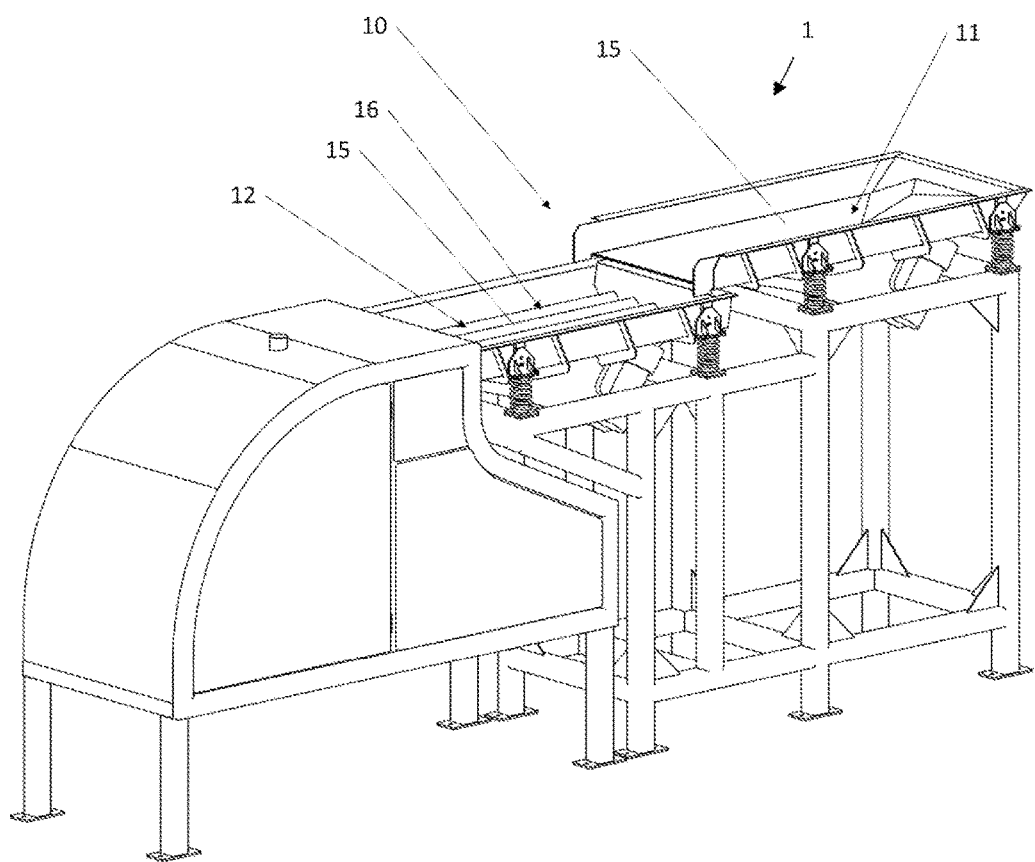
FIG. 3 shows a schematic perspective view of a system according to an embodiment of the invention.

FIGS. 3 to 7 show various views of a further embodiment of the system 1 according to the invention. As shown in FIG. 3, the feeder means 10 may be implemented by two vibration feeders 11, 12, wherein the upstream vibration feeder 11 feeds pieces of material 2 towards and onto the downstream vibration feeder 12. The downstream vibration feeder 12 may have a corrugated feeding surface 15 forming channels 16 as described above. The upstream vibration feeder 11 may, according to embodiments, have an at least substantially plane/planar feeding surface 15. The feeding surface 15 may be inclined, e.g. to form a slope inclined in the downstream direction. The upstream vibration feeder 11 may be operated with a lower vibration frequency and/or a lower vibration amplitude than the downstream vibration feeder 12.

FIG. 4 shows a sectional view of the system 1 shown in FIG. 3. As is apparent, the downstream vibration feeder 12 transports a piece of material 2 (not shown in FIG. 4) onto the upper portion 21 of the chute 20. Then, the piece of material 2 may slide down the chute 20 driven at least partially by gravity downwards towards the lower edge 22 of the chute 20. Depending on the size of the piece of material 2, when the piece of material 2 is projecting over the lower edge 22 of the chute 20 or has fallen from the chute 20 and is airborne, it is hit by the laser beam 35 generated by the laser device 30. The laser beam 35 that is incident on the piece of material 2 causes an emission indicative of the chemical composition of the piece of material 2 from the piece of material 2. Said emission is detected and analyzed by the spectrometer 40. A controller device 60 (not shown in FIG. 4) receives an output from the spectrometer 40 and determines based on at least one sorting criterion into which fraction the piece of material 2 should be sorted in. Based on the result of the determination, the sorting device 50 is operated by the controller device 60 to impart an impulse on the piece of material 2 that has fallen from the lower edge 22 of the chute 20 and is airborne. In FIG. 4, two arrows are shown that schematically show a trajectory of the piece of material 2 depending on the speed of the piece of material 2 on the chute 20. As is apparent, according to embodiments of the system 1, a focus point of the laser beam 35 may be chosen such that it is in a region neighboring the lower edge 22 of the chute 20 where the trajectories of the pieces of material 2 are generally similar even for different speeds.

FIG. 5 shows a partial perspective view of the system 1 according to the invention. For clarity, the feeding means 10 is not shown. As is apparent from FIG. 5, the system 1 comprises several pairs of laser device 30 and spectrometer 40, wherein the pairs form a line in the width direction of the chute 20 (and the feeder means 10 that is not shown). The sorting device 50 is implemented as an air gun/blower having several selectively controllable air outlets that can selectively impart a respective impulse on several pieces of material 2 simultaneously based on a control by the control device 60.

FIG. 6 shows a side view of the view shown in FIG. 5 and an enlarged view of FIG. 4. A piece of material 2 is shown that has just fallen from the lower edge 22 of the chute 20 and is airborne. The laser beam 35 is incident on the piece of material 2 to generate an emission that allows analyzing the chemical composition of the piece of material 2 and sorting the piece of material 2.

Figure 7:
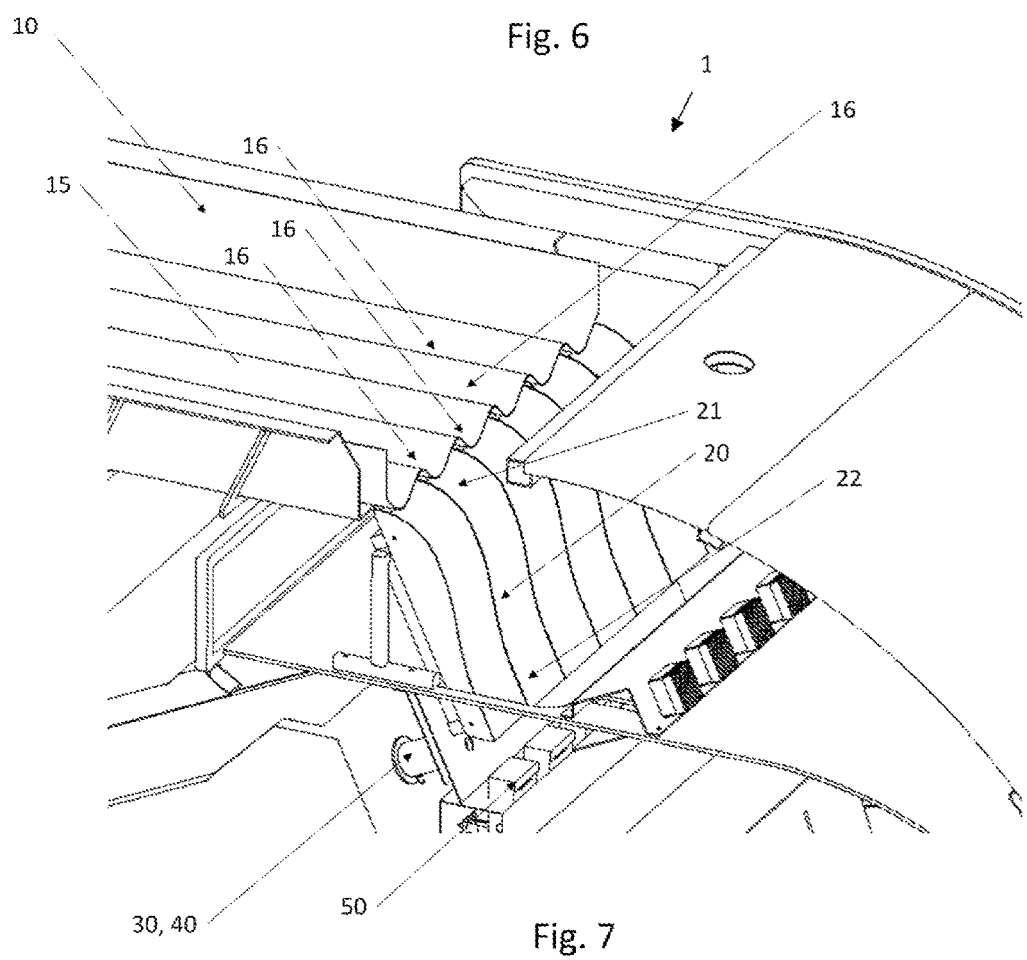
FIG. 7 shows a partial perspective view of a system according to an embodiment of the invention that shows guiding slides and a feeder means implemented as a vibration feeder with a corrugated feeding surface.
Figure 8:
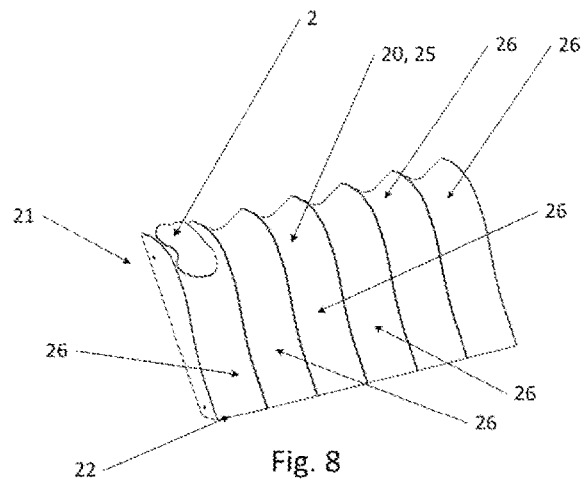
Figure 9:
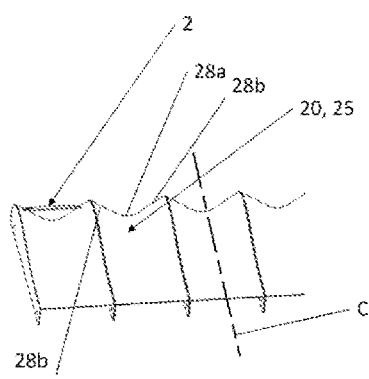
Figure 10:
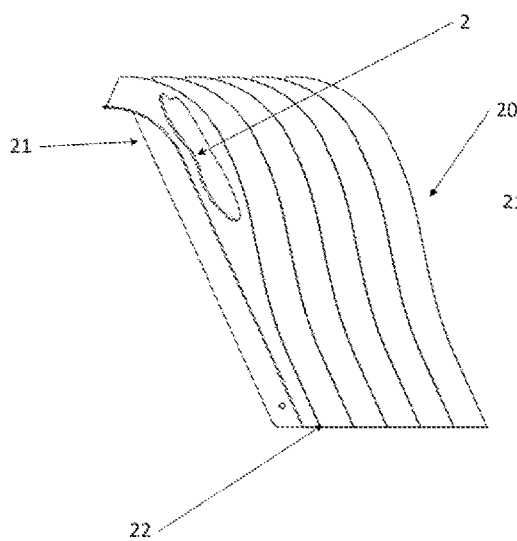
Figure 11:
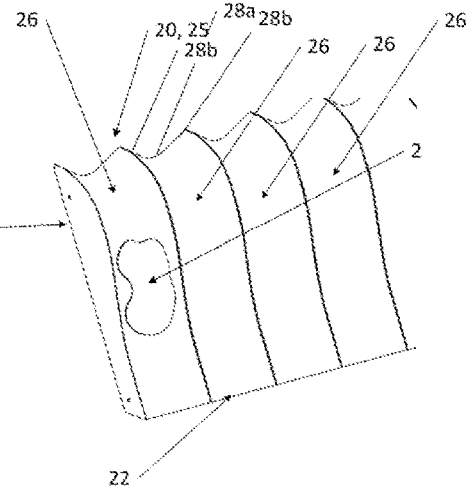

FIG. 7 shows an enlarged perspective view of a system 1 according to the invention. The corrugated shape of the feeding surface 15 forming channels 16 is visible. Each channel 16 has a centerline that is parallel to a direction of the channel 16. It is apparent that the feeder means 10 transports pieces of material 2 onto the upper portion 21 of the chute 20 along the channels 16 formed by the corrugated feeding surface 15. It is further apparent that the chute 20 forms a guiding slide 25 having a geometry that will be described in the following. It has been found that when the chute 20 is implemented as a guiding slide 25 having a configuration as described below, the efficiency of the system 1 can be significantly improved as pieces of material 2, even if they have an inhomogeneous form (such as pieces of aluminium scrap may have) can be efficiently transported to the laser beam 35. Further, the geometry of the chute 20 implemented as a guiding slide 25 allows higher transport speeds of the pieces of material 2, and therefore a higher throughput of the system 1, as it has been found that the pieces of material 2 are less likely to get lifted by aerodynamic forces that may cause pieces of material 2 to fly off the chute and or to block the chute 20 when a chute 20 implemented as a guiding slide 25 is used.

FIGS. 8 to 15 show detailed views of the chute 20 implemented as a guiding slide 25. The guiding slide 25 may define at least one channel 26 along which pieces of material 2 are guided from the upper portion 20 to the lower edge 21. Although in FIGS. 8 to 15 a guiding slide 25 having six channels 26 is shown, the guiding slide 25 may also have less channels 26 (e.g. only one channel 26) or more channels 26, e.g. seven, eight, nine or ten or more channels 26.

Each channel 26 may have a length direction L (see e.g. FIG. 14 for a schematic indication) extending from the upper portion 21 to the lower edge 22 that generally describes the path of a piece of material 2 that moves from the upper portion 21 to the lower edge 22. Each channel 26 may further have a width direction W that is perpendicular to the length direction L, see e.g. FIG. 14. As can be seen e.g. from FIG. 12 or FIG. 15 that show a section of a channel 26 along the length direction L and through the bottom or trough 28a of a channel 26, the channel 26 has, in the length direction L, a convex shape 27a in the upper portion 21 followed by a straight portion 27b between the convex shape and the lower edge 22. Said straight portion 27b may form the lower edge 22 of the guiding slide 25.

In a section in the width direction W of the guiding slide 25 that is perpendicular to the length direction L, the channel 26 may have a curvature, e.g. a curvature corresponding to a V- or U-profile or to a different profile, in the upper portion 21 of the chute 20. The channel 26 may define a flat configuration in a width section at the lower edge 22 of the chute 20.

That is, the channel 26 in a section along the length direction L comprises a convex portion 27a in the upper portion 21 of the chute 20 followed by a straight portion 27b between the convex portion 27a and the lower edge 22. For example with reference to FIG. 14, the channel 26 in a section along the width direction W in the upper portion 21 may have a profile shape with a trough 28a and two side walls 28b having a first height h1, and the channel 26 in a section along the width direction between the upper portion 21 and the lower edge 22 may have a profile shape with a trough 28a and two side walls 28b having a second height h2, wherein the first height h1 may be larger than the second height h2. In other words, the shape of the channel 26 seen in a width section may gradually change from a profile defining a trough 28a and sidewalls 28b to a flat configuration when going from the upper portion 21 of the chute 20 towards the lower edge 22 of the chute as shown e.g. FIGS. 12 and 13.

The profile of the chute 20 in the width section may be steady/continuous with a gradually changing curvature. The shape of the chute 20 in the length section may be steady/continuous with a gradually changing curvature With further reference to FIGS. 8 to 15, a piece of material 2 is guided down an individual channel 26 and prevented from skewing or rotating from a centerline of the channel 26. A virtual line C (FIG. 9) congruent with the centerline that is an imaginary extension of the centerline C of the channel 26 may intersect the path of the laser beam 35. As is apparent e.g. from FIG. 9, large pieces of material 2 can bridge between the sides 28b of the channel 26 and will be guided down the center of the channel 26. As is apparent e.g. from FIG. 11, as the piece of material 2 moves down the channel 26 from the upper portion 21 of chute 20 to the lower edge 22 of the chute 20, the side walls 28b of the channel 26 gently flatten while still guiding the piece of material 2 down the center of the channel 26.

As is e.g. apparent from FIG. 12, the sidewalls 28b and the trough 28a of a channel 26 form a concave profile in a width section that may be open at the top side. As is apparent e.g. from FIGS. 13 and 15, as the piece of material 2 moves down the channel 26, the sidewalls 28b flatten and the piece of material 2 moves closer to the lower edge 22 that in this embodiment has a straight configuration, while still being guided along the centerline C of the channel 26. FIG. 14 shows a piece of material 2 that is exiting the chute 20 and the channel 26 directly at the focal point of the laser beam 35. When the chute 20 is implemented as a guiding slide 25 as described herein, all pieces of material 2 independent of the size thereof (thickness and diameter) will be hit by the laser beam 35 at the same position, and the piece of material 2 is stabilized (moving smoothly and controlled along the channel 26) by the geometry of the chute 20 implemented as guiding slide 25 as described herein. Further, the sculpted and smoothly flowing form of the guiding slide 25 going from a concave form to a flat surface (with respect to the width direction) that is aligned with a focal point of the laser beam 35 allows a precise and reliable measurement of the chemical composition of a piece of material 2, especially when it is a piece of aluminium from a plurality of pieces of aluminium with different sizes and thicknesses (e.g. aluminium scrap material).

A distance between the lower edge 22 of the chute 20 and the point of intersection between said virtual line C and the laser beam 35 may be between 1 and 50 mm, e.g. between 5 and 10 mm. In the width section, the channel 26 may be symmetrical with respect to a plane in which virtual line C lies.

With reference to the figures, the invention also provides a method for analyzing and sorting metal comprising supplying at least one piece of metal (e.g. a piece of aluminium scrap that is part of a plurality of aluminium scrap pieces to be sorted having different diameters and/or thicknesses) 2 to and onto a feeding surface 15 of a feeder means 10, transporting the at least one piece of metal 2 on the feeding surface 15 towards and onto an upper portion 21 of a chute 20 using the feeder means 10, sliding the at least one piece of metal 2 on the chute 20 from the upper portion 21 of the chute 20 towards an lower edge 22 of the chute 20 by using a gravitational force (at least as a part of the total force that causes the piece of material to slide along the chute 20), providing a laser beam 35 such that the laser beam 35 is incident on a part of the at least one piece of metal 2 that is protruding over the lower edge 22 of the chute 20, or such that the laser beam 35 is incident on the at least one piece of metal 2 when the at least one piece of metal 2 has fallen from the chute 20 via the lower edge 22 of the chute 20, generating an emission from the at least one piece of metal 2 using the laser beam 35, detecting the emission, determining to which fraction of at least two fractions F1, F2 the at least one piece of metal 2 corresponds based on the detecting and at least one sorting criterion, and sorting the piece of metal 2 into one of the at least two fraction based on the result of the determining step.

The method may further comprise a pretreatment step comprising pretreating the aluminium scrap material before it is supplied to the feeder means 10 by sorting such that the aluminium scrap material 2 has a maximum diameter between 5 mm and 200 mm, e.g. 10 and 150 mm, optionally between 10 mm and 40 mm. It has been found that pieces 2 of the mentioned size result in an optimized analyzing and sorting performance.

The transporting may comprise transporting at least two pieces of material and changing a relative distance between the at least two pieces of material on the feeding surface while transporting the at least two pieces of material, e.g. by using a vibration feeder as feeder means 10. As mentioned above, this may avoid overlap of pieces of material 2 by singulating/separating pieces of material 2.

It is noted that features that are described with reference to the system 1 also apply correspondingly for the described method and vice versa. All embodiments described herein can be combined with each other.

The invention claimed is:
1. A system for analyzing and sorting material comprising:
 a chute;
 a feeder means for transporting at least one piece of material along a feeding surface towards and onto an upper portion of the chute, wherein the at least one piece of material is slidable on the chute and off the chute via a lower edge of the chute;
 a sorting device operable to sort the at least one piece of material according to at least two fractions;
 a laser device configured to generate a laser beam that, when the laser beam is incident on the at least one piece of material, can produce an emission from the piece of material;
 a spectrometer configured to detect the emission from the at least one piece of material and to produce an output signal corresponding to the emission and indicative of a chemical composition of the at least one piece of material; and
 a controller device configured to receive the output signal and to operate the sorting device based on the output signal and at least one sorting criterion,
 wherein the laser device and the spectrometer are both positioned on a same side of the chute in a direction perpendicular to a transportation direction of the chute,
 wherein the laser device is configured to produce a laser beam that can be incident on the at least one piece of material when the at least one piece of material is at least partially protruding from the chute over the lower edge of the chute or has fallen off from the chute via the lower edge of the chute and is airborne,
 wherein the chute defines a channel configured to guide the at least one piece of material from the upper portion of the chute to the lower edge of the chute, wherein the channel includes a convex portion at the upper portion of the chute and a straight portion between the convex portion and the lower edge of the chute, and wherein the channel is configured such that an extension of a centerline thereof intersects a path of the laser beam.

2. The system according to claim 1, wherein the at least one piece of material comprises pieces of material and the feeder means is configured to change relative distances between the pieces of material on the feeding surface while transporting the pieces of material.

3. The system according to claim 2, wherein the feeder means comprises at least one vibration feeder.

4. The system according to claim 3, wherein the at least one vibration feeder comprises at least an upstream vibration feeder and a downstream vibration feeder, wherein the upstream vibration feeder is configured to transport the pieces of material towards and onto the downstream vibration feeder, wherein the downstream vibration feeder is configured to transport the pieces of material towards and onto the upper portion of the chute, wherein the feeding surface of the upstream vibration feeder is positioned on a higher level than the feeding surface of the downstream vibration feeder, and wherein the upstream vibration feeder is configured to be operated at a lower vibration frequency and/or amplitude than the downstream vibration feeder.

5. The system according to claim 4, wherein at least the feeding surface of the downstream vibration feeder has a corrugated shape that defines a plurality of channels.

6. The system according to claim 1, wherein the system does not comprise beam separation means or beam deflection means in the path of the laser beam between the laser device configured to generate the laser beam and the at least one piece of material on which the laser beam is incident.

7. The system according to claim 1, wherein the at least one piece of material is a piece of metal scrap.

8. The system according to claim 7, wherein the piece of metal scrap is a piece of 5xxx or 6xxx series aluminum having a diameter of more than 5 mm and less than 200 mm.

9. The system according to claim 7, wherein the piece of metal scrap is a piece of 5xxx or 6xxx series aluminum having a diameter of more than 10 mm and less than 150 mm.

10. The system according to claim 7, wherein the piece of metal scrap is a piece of 5xxx or 6xxx series aluminum having a diameter of more than 10 mm and less than 40 mm.

11. The system according to claim 1, wherein the laser device, the spectrometer and the controller device define a LIBS system and are housed in a common housing.

12. The system according to claim 1, wherein the laser beam, after being generated by the laser device, extends upwards with an angle of between 0 and 90 degrees with respect to a horizontal line.

13. The system according to claim 1, wherein the laser beam does not propagate through an opening or aperture in the chute.

14. The system according to claim 1, wherein the chute is defines a length direction between the upper portion of the chute and the lower edge of the chute and a width direction perpendicular thereto, and wherein the channel in a section along the width direction in the upper portion of the chute has a profile shape with a trough and two side walls having a first height, and wherein the channel in a section along the width direction between the upper portion of the chute and the lower edge of the chute has a profile shape with a trough and two side walls having a second height, wherein the first height is larger than the second height.

15. The system according to claim 14, wherein the channel in a section along the width direction through the lower edge of the chute has a straight shape that is at least substantially horizontal.

16. The system according to claim 1, wherein the sorting device is configured to impart an impulse on the at least one piece of material by using compressed air or by using a physical contact with a mechanical device, and wherein the system further comprises a separator positioned spatially between two bins or conveyors corresponding to two of the at least two fractions.

17. The system according to claim 1, wherein a downstream end of the feeding surface has a corrugated shape that defines a plurality of channels.

18. A method for analyzing and sorting material comprising:

supplying at least one piece of material to and onto a feeding surface of a feeder means;

transporting the at least one piece of material on the feeding surface towards and onto an upper portion of a chute using the feeder means;

sliding the at least one piece of material on the chute which defines a channel which guides the at least one piece of material from the upper portion of the chute towards a lower edge of the chute by at least partially using a gravitational force, wherein the channel includes a convex portion at the upper portion of the chute and a straight portion between the convex portion and the lower edge of the chute;

providing a laser beam such that the laser beam is incident on a part of the at least one piece of material that is protruding over the lower edge of the chute, or such that the laser beam is incident on the at least one piece of material when the at least one piece of material has fallen from the chute via the lower edge of the chute and is airborne, wherein an extension of a centerline of the channel intersects a path of the laser beam;

generating an emission from the at least one piece of material using the laser beam, and detecting the emission;

determining to which fraction of at least two fractions the at least one piece of material corresponds based on the detecting and at least one sorting criterion; and sorting the at least one piece of material into one of the at least two fractions based on the determining.

19. The method according to claim 18, wherein the at least one piece of material is aluminum scrap material, and the method further comprises pre-treating the aluminum scrap material by sorting such that the aluminum scrap material has a maximum diameter between 5 mm and 200 mm.

20. The method according to claim 18, wherein the at least one piece of material comprises at least two pieces of material and the transporting comprises changing a relative distance between the at least two pieces of material on the feeding surface while transporting the at least two pieces of material.

* * * * *